United States Patent
Zirps et al.

[11] Patent Number: 5,851,212
[45] Date of Patent: Dec. 22, 1998

[54] SURGICAL INSTRUMENT

[75] Inventors: Christopher T. Zirps, Milton; Newton E. Mack, Somerville, both of Mass.

[73] Assignee: Endius Incorporated, Plainville, Mass.

[21] Appl. No.: 872,832

[22] Filed: Jun. 11, 1997

[51] Int. Cl.⁶ .................................................. A61B 17/32
[52] U.S. Cl. .................. 606/167; 606/167; 606/174; 606/180; 604/95
[58] Field of Search .................. 606/79, 83, 167, 606/170, 174, 180, 205, 206, 207, 208; 604/95; 600/564

[56] References Cited

U.S. PATENT DOCUMENTS

| | | |
|---|---|---|
| 3,470,876 | 10/1969 | Barchilon . |
| 3,521,620 | 7/1970 | Cook . |
| 3,605,725 | 9/1971 | Bentov . |
| 5,378,234 | 1/1995 | Hammerslag et al. .................. 604/95 |
| 5,669,926 | 9/1997 | Aust et al. .............................. 606/170 |

FOREIGN PATENT DOCUMENTS

| | | |
|---|---|---|
| 0301288A1 | 2/1989 | European Pat. Off. . |
| 2662778 | 8/1987 | France . |
| 3920706A1 | 1/1991 | Germany . |
| 4136861A1 | 5/1993 | Germany . |
| 4204051A1 | 8/1993 | Germany . |
| 09300048 | 1/1993 | WIPO . |
| 09304634 | 3/1993 | WIPO . |
| 09320760 | 10/1993 | WIPO . |

*Primary Examiner*—Michael Buiz
*Assistant Examiner*—David O. Reip
*Attorney, Agent, or Firm*—Tarolli, Sundheim, Covell, Tummino & Szabo

[57] ABSTRACT

A surgical instrument (10) includes a handle (12), a rigid stem section (20) extending from the handle, and a flexible stem section (24) extending from the rigid stem section. A surgical tool (30) connected with a distal end of the flexible stem section (24) includes a movable part (34). The flexible stem section (24) comprises a bendable outer tubular member (50) and a bendable inner tubular member (90) slidable within the outer tubular member. The inner tubular member (90) has a neutral axis of bending (100) spaced apart from the neutral axis of bending (68) of the outer tubular member (50). The flexible stem section (24) is movable between a plurality of orientations relative to an axis (48) in response to relative sliding movement between the inner and outer tubular members (90, 50).

19 Claims, 5 Drawing Sheets

U.S. Patent  Dec. 22, 1998  Sheet 1 of 5  5,851,212
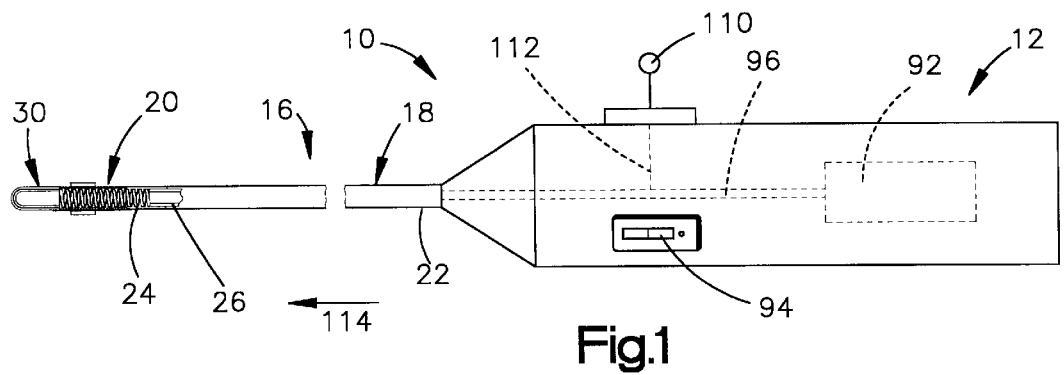
Fig.1
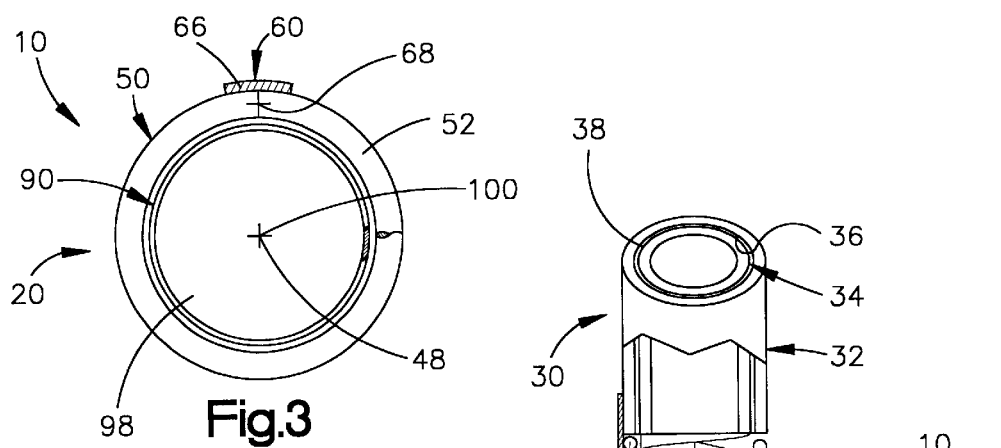
Fig.3
Fig.4
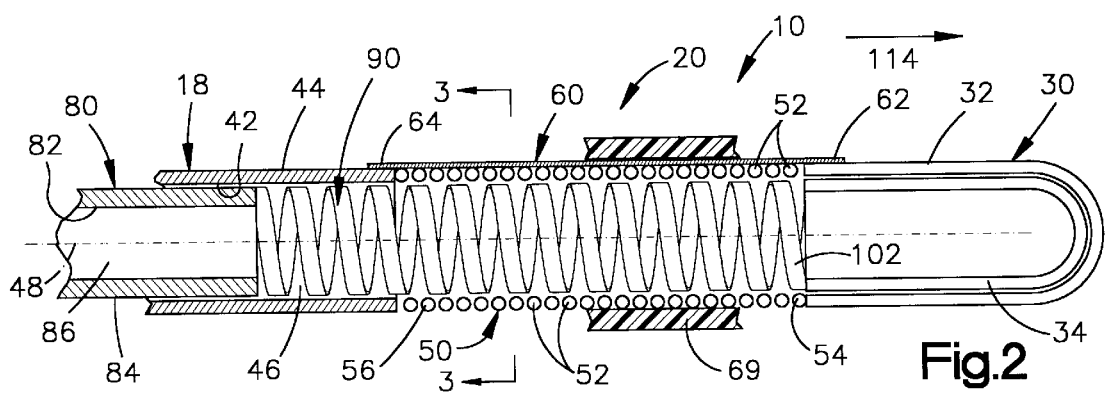
Fig.2

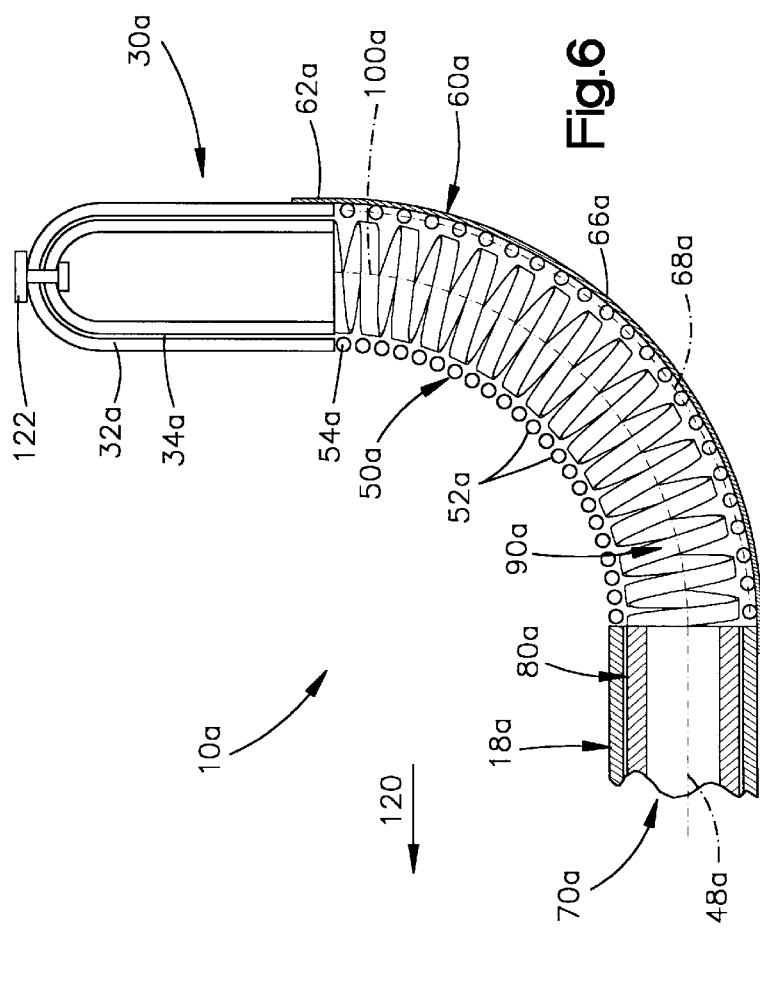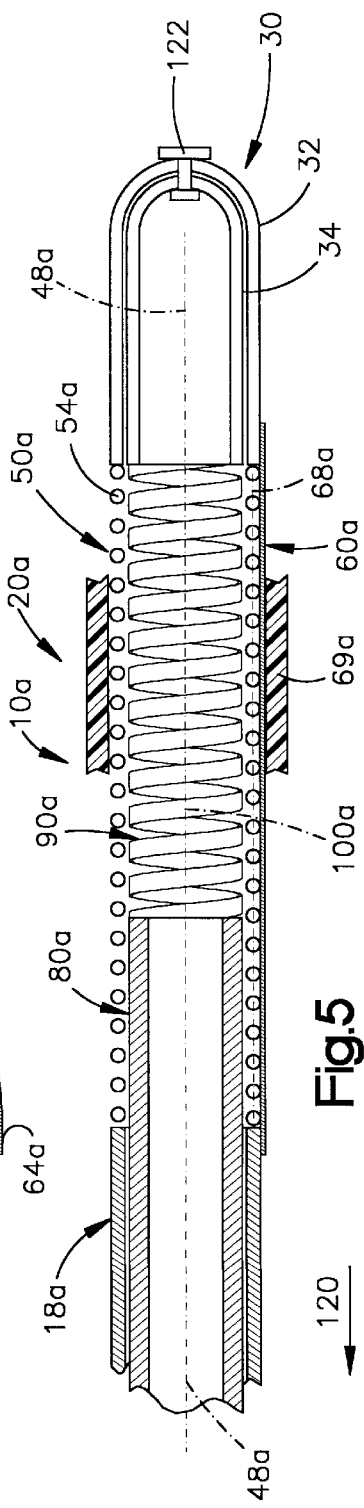

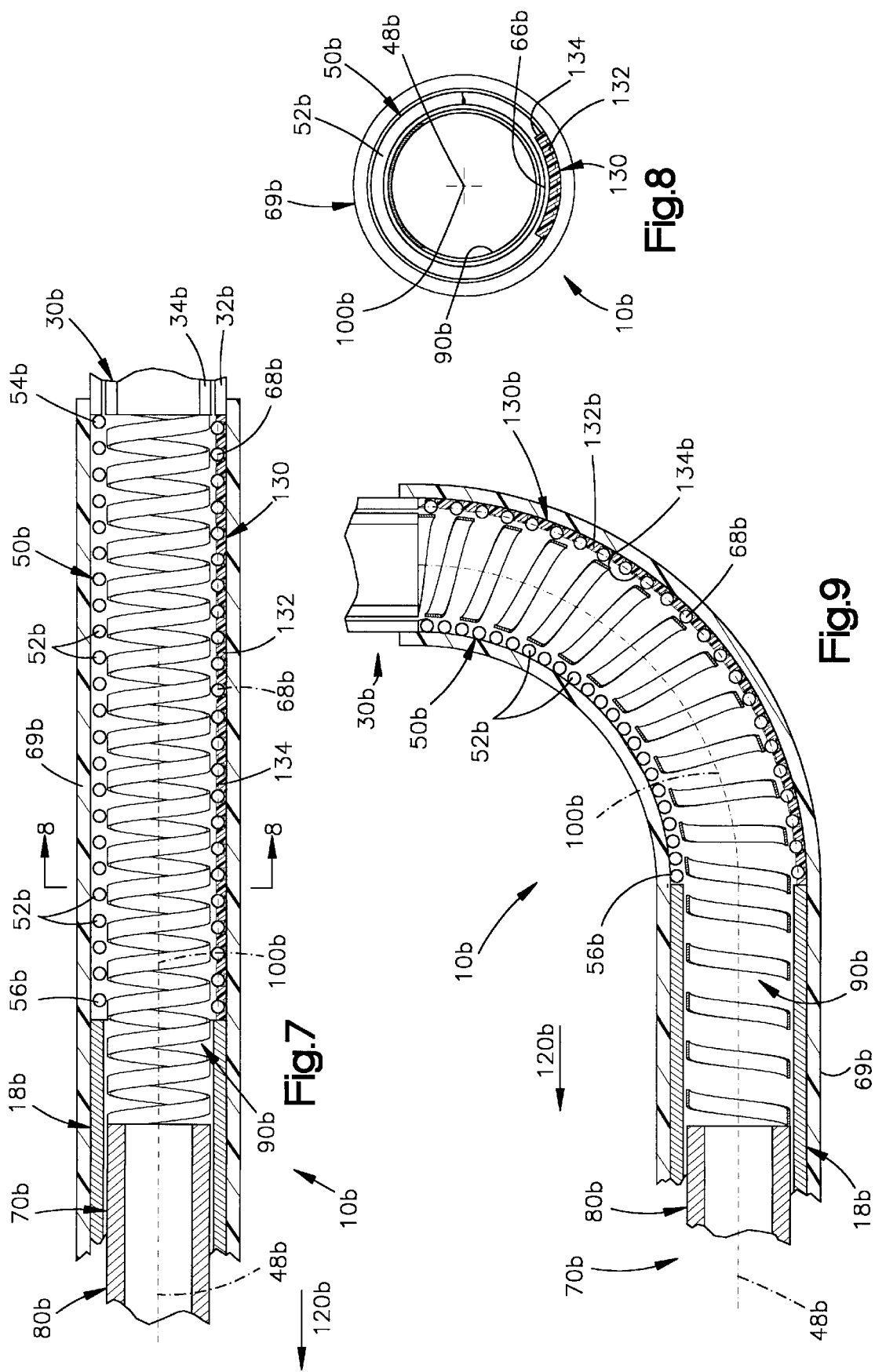

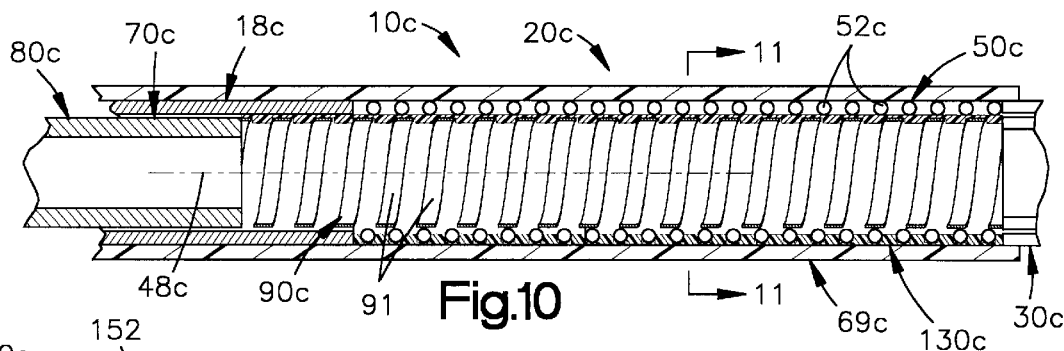
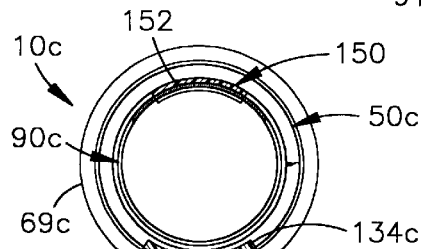
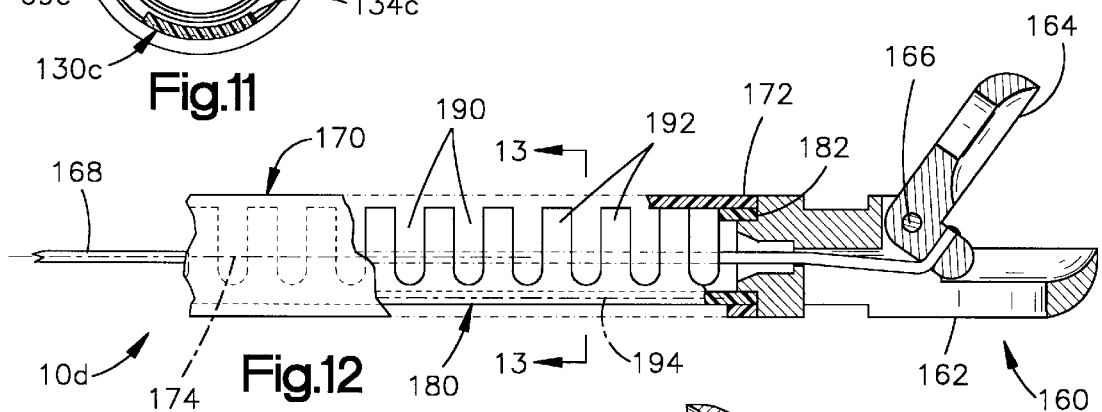
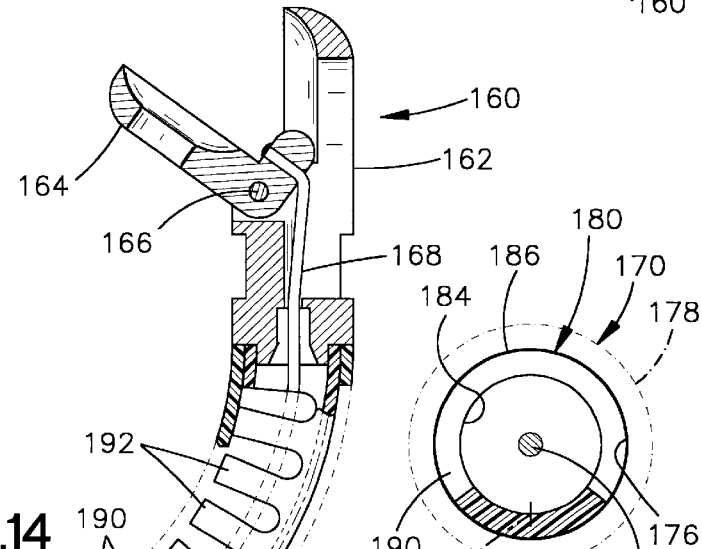
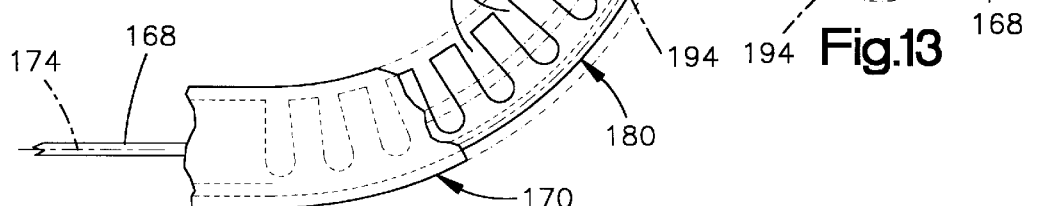

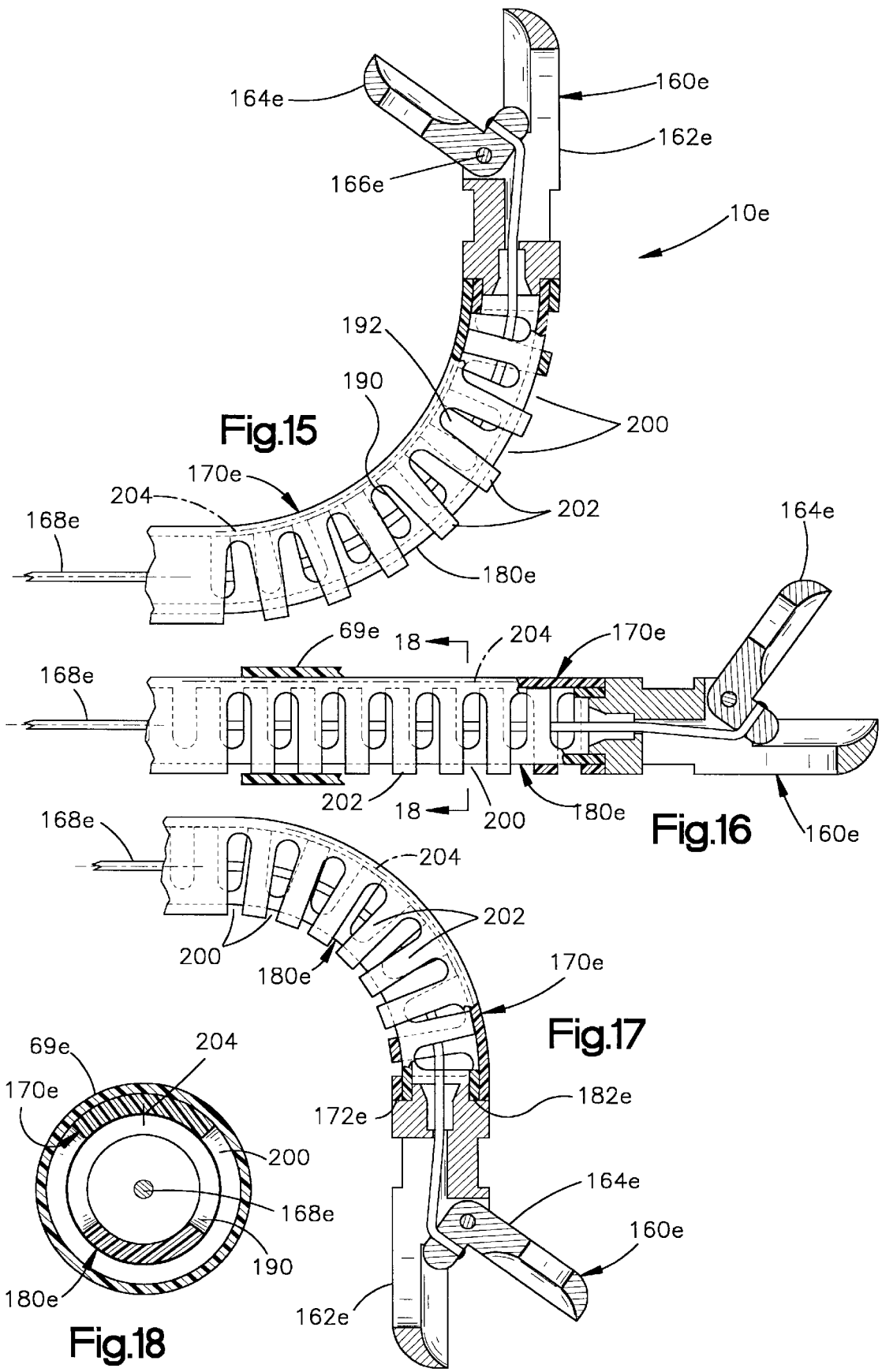

SURGICAL INSTRUMENT

BACKGROUND OF THE INVENTION

The present invention relates to a surgical instrument and, more particularly, to an endoscopic surgical instrument which may be used for cutting and/or removal of tissue.

SUMMARY OF THE INVENTION

The present invention is a surgical instrument including a handle, a rigid stem section extending from the handle and defining a longitudinal axis of said surgical instrument, and a flexible stem section extending from the rigid stem section. A surgical tool connected with a distal end of the flexible stem section includes a movable part. The flexible stem section comprises a bendable outer tubular member and a bendable inner tubular member slidable within the outer tubular member. The outer tubular member has a neutral axis of bending. The inner tubular member has a neutral axis of bending spaced apart from the neutral axis of bending of the outer tubular member. The flexible stem section is movable between a plurality of orientations relative to the axis in response to relative sliding movement between the inner and outer tubular members.

In a preferred embodiment, the tubular members are both coiled springs.

BRIEF DESCRIPTION OF THE DRAWINGS

Further features of the present invention will become apparent to those skilled in the art to which the present invention relates from reading the following specification with reference to the accompanying drawings, in which:

FIG. 1 is a side elevational view, partly in section, of a surgical instrument constructed in accordance with a first embodiment of the present invention;

FIG. 2 is an enlarged view of a flexible stem section of the surgical instrument of FIG. 1, shown in a linear condition;

FIG. 3 is a view taken generally along line 3—3 of FIG. 2;

FIG. 4 is a view similar to FIG. 2 of the flexible stem section of the surgical instrument of FIG. 1, shown in a curved condition;

FIG. 5 is a view similar to FIG. 2 of the flexible stem section of a surgical instrument constructed in accordance with a second embodiment of the present invention, shown in a linear condition;

FIG. 6 is a view similar to FIG. 5 of the flexible stem section of the surgical instrument of FIG. 5, shown in a curved condition;

FIG. 7 is a view similar to FIG. 2 of the flexible stem section of a surgical instrument constructed in accordance with a third embodiment of the present invention, shown in a linear condition;

FIG. 8 is a view taken generally along line 8—8 of FIG. 7;

FIG. 9 is a view similar to FIG. 7 of the flexible stem section of the surgical instrument of FIG. 9, shown in a curved condition;

FIG. 10 is a view similar to FIG. 2 of the flexible stem section of a surgical instrument constructed in accordance with a fourth embodiment of the present invention, shown in a linear condition;

FIG. 11 is a view taken generally along line 11—11 of FIG. 10;

FIG. 12 is a view similar to FIG. 2 of the flexible stem section of a surgical instrument constructed in accordance with a fifth embodiment of the present invention, shown in a linear condition;

FIG. 13 is a view taken generally along line 13—13 of FIG. 12;

FIG. 14 is a view similar to FIG. 12 showing the flexible stem section in a curved condition;

FIG. 15 is a view similar to FIG. 2 of the flexible stem section of a surgical instrument constructed in accordance with a sixth embodiment of the present invention, shown in a curved condition;

FIG. 16 is a view similar to FIG. 15 showing the flexible stem section in a linear condition;

FIG. 17 is a view similar to FIG. 15 showing the flexible stem section in a condition curved in a different direction; and FIG. 18 is a view taken generally along line 18—18 of FIG. 16.

DESCRIPTION OF PREFERRED EMBODIMENTS

The present invention relates to a surgical instrument and in particular to an endoscopic surgical instrument which may be used for cutting and/or removal of tissue. The present invention is applicable to various surgical instrument constructions. As representative of the present invention, FIG. 1 illustrates a surgical instrument 10.

FIGS. 1–8 illustrate a surgical instrument 10 which is constructed in accordance with a first embodiment of the present invention. The surgical instrument 10 includes a handle 12. A stem section 16 is connected with and projects from the handle 12. The stem section 16 includes a first stem section or rigid stem section 18 and a second stem section or flexible stem section 20.

A proximal end portion 22 of the first stem section 18 is fixed to the handle 12. A proximal end portion 24 of the second stem section 20 is connected with a distal end portion 26 of the first stem section 18. A rotary cutter assembly or shaver assembly 30 is connected with a distal end portion 31 of the second stem section 20.

The shaver assembly 30 (FIGS. 2 and 3) includes a fixed outer part 32 and a rotatable inner part 34. The outer part 32 of the shaver assembly 30 has a generally cylindrical, tubular configuration with a first cutting edge 36. The inner part 34 of the shaver assembly 30 has a generally cylindrical configuration and is rotatable within the outer part 32 of the shaver assembly. The inner part 34 of the shaver assembly 30 has a second cutting edge 38. The shaver assembly 30 is preferably made from metal.

The rigid stem section 18 is substantially non-bendable during use of the surgical instrument 10. The rigid stem section 18 has a tubular cylindrical configuration including parallel inner and outer surfaces 42 and 44 (FIG. 2). The inner surface 42 defines a cylindrical central passage 46. The rigid stem section 18 has a longitudinal central axis 48 (FIGS. 2 and 4) which forms a longitudinal central axis of the surgical instrument 10.

The flexible stem section 20 of the surgical instrument 10 includes an outer tubular member in the form of an extension spring 50 for supporting the non-rotating outer part 32 of the shaver assembly 30 on the rigid stem section 18 of the surgical instrument. In the illustrated embodiment, the spring 50 is a coiled spring, specifically, a cylindrical helical spring of circular cross section, made from metal wire. The spring 50 is preferably made from stainless steel.

The spring 50 includes a plurality of coils 52 spaced along the length of the flexible stein section 20. A first end portion 54 of the spring 50 is secured, as by welding, to the non-rotating outer part 32 of the shaver assembly 30. An opposite second end portion 56 of the spring is secured, as by welding, to the rigid stem section 18 of the surgical instrument 10.

The flexible stem section also includes a metal strap 60. The strap 60 extends along the outer periphery of the spring 50 and overlies the coils 52 of the spring. The strap 60 is welded to the spring 50 when the spring is in a free or unextended condition, that is, when the coils 52 of the spring are very closely spaced or in abutting engagement with each other and the spring is not compressible axially. The extension spring 50 is in a free or unstressed condition when the flexible stem section 24 is in a linear condition as shown in FIG. 2.

The strap 60 is fixed to the spring 50 at one particular location 66 (FIG. 3) around the circumference of the spring 50. In the illustrated embodiment, the strap 60 has a circumferential extent of about 25° about the axis 48. A first end portion 62 of the strap 60 is also welded to the non-rotating outer part 32 of the shaver assembly 30. An opposite second end portion 64 of the strap 60 is welded to the rigid stem section 18 of the surgical instrument 10.

The strap 60 is inextensible. Thus, the neutral axis of bending of the spring 50 (designated generally 68 in FIG. 3) is located about at the strap 60, not at the radial center of the spring. When the spring 50 is bent or curved out of the linear condition shown in FIG. 2, the spacing does not change between the coil portions to which the strap 60 is fixed. The welding of the strap 60 to the coils 52 of the spring 50 prevents the coils of the spring from moving apart, or closer together, during bending movement of the spring, at the one particular location 66 on the circumference of the spring. As a result, the one circumferential portion or "side" 66 of the spring 50 to which the strap 60 is fixed can not extend.

The spring 50 provides a self-centering effect for the flexible stem section 20 of the surgical instrument 10. Specifically, when the flexible stem section 20 of the instrument 10 is bent to a condition off the axis 48, as described below, the resilience provided by the spring 50 returns the flexible stem section to its linear position upon release of the bending force.

The surgical instrument 10 preferably includes a plastic outer sheath, a fragment of which is shown at 69 in FIG. 3. The sheath 69 is in the form of a shrink wrap which overlies the spring 50 and the strap 60. The sheath 69 seals the openings between adjacent coils 52 of the spring 50. The sheath 69 is, for clarity, shown with an exaggerated thickness in FIG. 2.

The surgical instrument 10 includes a drive shaft 70 for effecting rotation of the inner shaver part 34. The drive shaft 70 includes a rigid portion 80 and a flexible portion 90.

The rigid portion 80 of the drive shaft 70 is disposed in the central passage 46 of the rigid stem section 18. The rigid portion 80 of the drive shaft 70 is a cylindrical metal tube which has parallel cylindrical inner and outer surfaces 82 and 84. The inner surface 82 of the rigid portion 80 of the drive shaft 70 defines a central passage 86. The rigid portion 80 of the drive shaft 70 is rotatable within the rigid stem section 18 relative to the rigid stem section, about the longitudinal axis 48.

The surgical instrument 10 includes a suitable electric motor indicated schematically at 92 (FIG. 1) in the handle 12, for effecting rotation of the drive shaft 70. The motor 92 could, alternatively, be part of a control unit separate from the handle and connected with the handle through an electric cord. Also on the handle 12 is a switch indicated schematically at 94 for controlling operation of the motor 92.

An output shaft indicated schematically at 96 extends between the motor 92 and the rigid portion 80 of the drive shaft 70. The output shaft 96 is rotatable about the longitudinal central axis 48 by operation of the motor 92. The rigid portion 80 of the drive shaft 70 is, thereby, rotatable about the longitudinal central axis 48 by operation of the motor 92.

The flexible portion 90 of the drive shaft 70 is disposed within the flexible stem section 20 of the surgical instrument 10, that is, radially inward of the extension spring 50. The flexible portion 90 of the drive shaft 70 forms an inner tubular member or portion of the flexible stem section 20 of the surgical instrument 10. The flexible portion 90 of the drive shaft 70 is preferably formed as a helical coiled spring, preferably made from metal having a rectangular cross-sectional configuration, but could alternatively be formed in a different manner. The flexible portion 90 of the drive shaft 70 has an axially extending, central passage 98.

The flexible portion 90 of the drive shaft 70 has a uniform configuration around its circumference. The neutral axis of bending (designated 100 in FIG. 3) of the flexible portion 90 of the drive shaft 70 extends along the radial center of the flexible portion 90. Thus, the neutral axis of bending 100 of the flexible portion 90 of the drive shaft 70 is spaced apart from the neutral axis of bending 68 of the outer tubular member or spring 50.

The rotatable inner part 34 of the shaver assembly 30 is secured to a distal end 102 of the flexible portion 90 of the drive shaft 70. The flexible portion 90 of the drive shaft 70 is capable of transmitting rotational force from the rigid portion 80 of the drive shaft to the rotatable inner part 34 of the shaver assembly 30.

Upon actuation of the motor 90, the output shaft 96 and the drive shaft 70 are driven for rotation about the axis 48. The inner part 34 of the shaver assembly 30 rotates relative to the outer part 32 of the shaver assembly. The second cutting edge 38 on the inner part 34 of the shaver assembly 30 cooperates with the first cutting edge 36 on the outer part 32 of the shaver assembly, in a known manner, to remove tissue.

The flexible portion 90 of the drive shaft 70, like the extension spring 50, provides a self-centering effect for the flexible stem section 20 of the surgical instrument 10. Specifically, when the flexible stem section 20 of the instrument 10 is bent to a condition off the axis 48, as described below, the resilience provided by the flexible portion 90 of the drive shaft 70 helps to return the flexible stem section to its linear position upon release of the bending force.

During use of the surgical instrument 10, it is preferable to convey away from the shaver assembly 30 tissue which is removed from between vertebra or other locations. Accordingly, a suction pump (not shown) is preferably connected with the instrument handle 12. Suction is applied to the shaver assembly 30 through the central passage 86 in the rigid portion 80 of the drive shaft 70 and through the central passage 98 in the flexible portion 90 of the drive shaft. The suction draws or pulls tissue from the area immediately adjacent to the shaver assembly 30 back through the center of the flexible portion 90 of the drive shaft 70 and through the center of the rigid portion 80 of the drive shaft, to a point at the handle 12 where it can be removed.

In addition, water or other fluid can be utilized to irrigate the area where tissue is removed by the shaver assembly 30.

The irrigation fluid can be conducted through the central passage 86 in the rigid portion 80 of the drive shaft 70 and through the central passage 98 in the flexible portion 90 of the drive shaft, to the shaver assembly 30.

Other known types of rotatable tissue cutting devices may be substituted for the shaver assembly 30. Thus, a generally spherical rotatable burr or router may be used to abrade tissue. The particular type of shaver or shaver assembly which is connected with the flexible stem section 20 will depend upon the surgical operation to be performed.

To effect bending movement of the flexible stem section 20, the actuator assembly 14 of the surgical instrument includes a deflection control lever 110 (FIG. 1) which projects from the handle 12. The deflection control lever 110 is supported for pivotal movement relative to the handle 12. The deflection control lever 110 is operatively connected in a known manner, such as by suitable linkage indicated schematically at 112, with the motor 92, the output shaft 96, or the rigid portion 80 of the drive shaft 70. The control lever 110 is manually operable to move the rigid portion 80 of the drive shaft 70 axially relative to the rigid stem section 18.

When the lever 110 is moved in a first direction, the rigid portion 80 of the drive shaft 70 is urged to move outwardly, that is, in a direction away from the handle 12 as indicated by the arrow 114 in FIGS. 1, 2 and 4. The rigid portion 80 of the drive shaft 70 moves relative to the rigid stem section 18. Specifically, the rigid portion 80 of the drive shaft 70 slides axially within the rigid stem section 18, from the position shown in FIG. 2 toward the position shown in FIG. 4.

The force of the axially moving drive shaft portion 80 is transmitted into the flexible portion 90 of the drive shaft 70 and thus to the inner part 34 of the shaver assembly 30. The axial force on the inner part 34 of the shaver assembly 30 acts on the outer part 32 of the shaver assembly. This force is transmitted through the outer part 32 of the shaver assembly 30 into the distal end portion 56 of the extension spring 50.

The axially outwardly directed force on the spring 50 causes the spring to attempt to extend. The spring 50 does extend, but not linearly. Instead, because the strap 60 places the neutral axis 68 of bending of the spring 50 away from the neutral axis 100 of bending of the flexible portion 90 of the drive shaft 70, the flexible stem section 20 bends as it extends, to the condition shown in FIG. 4.

The spacing between the coils 52 of the spring 50 does not change at the location 66 where they are attached to the strap 60. The spacing between the coils 52 of the spring 50 increases significantly at the opposite side of the spring. The spring 50 thus elongates along the outside of the arc of its bending.

The bending of the flexible stem section 20 causes the shaver assembly 30 to be moved to an orientation off the longitudinal central axis 48. The amount of bending movement of the flexible stem section 20, and, thus, the position or orientation of the shaver assembly 30, is controlled by the amount of relative axial displacement between the rigid stem section 18 and the rigid portion 80 of the drive shaft 70. If the rigid portion 80 of the drive shaft 70 is displaced axially relative to the rigid stem section 18 by a relatively small amount or distance, the amount of bending movement of the flexible stem section 20 is relatively small, and the shaver assembly 30 assumes an orientation relatively close to the longitudinal central axis 48. If, on the other hand, the rigid portion 80 of the drive shaft 70 is displaced axially relative to the rigid stem section 18 by a relatively large amount or distance, the amount of bending movement of the flexible stem section 20 is relatively large, and the shaver assembly 30 assumes an orientation relatively far from the longitudinal central axis 48.

In the illustrated embodiment, the shaver assembly 30 is selectively movable to any orientation up to 90° off the longitudinal central axis 48. It should be understood that the present invention is not limited to bending movement of 90.

Upon movement of the deflection control lever 110 to its initial position, the axial force on the drive shaft 70 is released. The resilience provided by the flexible stem section 20 returns the surgical instrument 10 to its linear position.

FIGS. 5 and 6 illustrate a surgical instrument 10*a* constructed in accordance with a second embodiment of the present invention. The surgical instrument 10*a* is generally similar in construction and operation to the surgical instrument 10 (FIGS. 1–4). Parts of the surgical instrument 10*a* which are the same as or similar to corresponding parts of the surgical instrument 10 are given the same reference numeral with the suffix "a" added for clarity.

In the surgical instrument 10*a*, a strap 60*a* is attached to a spring 50*a* whose coils are spaced apart from each other when the spring is in a free or unstressed condition. In this unactuated condition of the surgical instrument 10*a*, the flexible stem section 20*a* has a linear configuration as seen in FIG. 5. The rigid portion 80*a* of the drive shaft 70*a* projects from the rigid stem section 18*a*.

When the deflection control lever (not shown) of the surgical instrument 10*a* is actuated, the rigid portion 80*a* of the drive shaft 70*a* is pulled in a direction toward the handle, that is, to the left as viewed in FIGS. 5 and 6 and as indicated by the arrow 120. The rigid portion 80*a* of the drive shaft 70*a* slides axially within the rigid stem section 18*a*, from the position shown in FIG. 5 toward the position shown in FIG. 6.

The force of the axially moving drive shaft portion 80*a* is transmitted into the flexible portion 90*a* of the drive shaft 70*a* and thus to the inner part 34*a* of the shaver assembly 30. The axial force on the inner part 34*a* of the shaver assembly 30*a* is transmitted through a pivot pin 122 into the outer part 32*a* of the shaver assembly. This force is transmitted through the outer part 32*a* of the shaver assembly 30*a* into the distal end portion 54*a* of the spring 50*a*.

The axially inwardly directed force on the spring 50*a* attempts to compress the spring. The spring 50*a* does compress, but not linearly. Instead, because the strap 60*a* places the neutral axis of bending 68*a* of the spring 50*a* away from the neutral axis of bending 100*a* of the flexible portion 90*a* of the drive shaft 80*a*, the spring bends away from the strap as the spring compresses, assuming the bent condition shown in FIG. 6.

The strap 60*a* controls the spacing between the coils 52*a* of the spring 50*a*. Specifically, the spacing between the coils 52*a* of the spring 50*a* does not change at the location 66*a* where the coils are interconnected by the strap 60*a*. The spacing between the coils 52*a* of the spring 50*a* decreases significantly at the opposite side of the spring. The spring 50*a* shortens along the inside of the arc through which it bends.

The bending of the flexible stem 20*a* section causes the shaver assembly 30*a* to be moved to an orientation off the longitudinal central axis 48*a*. The amount of bending movement of the flexible stem section 20*a*, and, thus, the position or orientation of the shaver assembly 30*a*, is controlled by the amount of relative axial displacement between the rigid stem section 18*a* and the rigid portion 80*a* of the drive shaft 70*a*.

Upon movement of the deflection control lever to its initial position, the axial force on the drive shaft 70a is released. The resilience provided by the flexible stem section 20a including the flexible portion 90a of the drive shaft 70a help to return the surgical instrument 10a to its linear condition.

Because the coils 52a of the spring 50a are spaced apart when the surgical instrument 10a is in the linear condition shown in FIG. 5, the surgical instrument 10a can be directed to bend in the opposite direction also. Specifically, if the deflection control lever (not shown) of the surgical instrument 10a is actuated in the opposite direction, so that the rigid portion 80a of the drive shaft 70a is pushed in a direction away from the handle 12a, the flexible stem section 20a bends in the opposite direction from FIG. 6, that is, downward as viewed in FIG. 5. The spring 50a in this case elongates along the outside of the arc through which it bends.

FIGS. 7–9 illustrate a surgical instrument 10b constructed in accordance with a third embodiment of the present invention. The surgical instrument 10b is generally similar in construction and operation to the surgical instrument 10a (FIGS. 5–6). Parts of the surgical instrument 10b which are the same as or similar to corresponding parts of the surgical instrument 10a are given the same reference numeral with the suffix "b" added for clarity.

In the surgical instrument 10b, a spacer 130 is substituted for the strap 60b. The spacer 130 is an elongate member, preferably made from plastic, having a main body portion 132 which extends along the outer periphery of the coils 52b of the spring 50b. The spacer 130 is held in position relative to the spring 50b by a sheath 69b. The spacer 130 is disposed at one particular location 66b around the circumference of the spring. In the illustrated embodiment, the spacer 130 has a circumferential extent of about 25° about the axis 48b.

A plurality of projecting portions 134 of the spacer 130 in the form of small ribs or fingers extend radially inward from the main body portion 112 of the spacer. Each one of the projecting portions 134 of the spacer 130 is disposed between, and separates, a pair of adjacent coils 52b of the spring 50b. The spacer 130 thus controls the spacing between the coils 52b of the spring 50b, as the strap 60b controls the spacing of the coils 52a of the spring 50a.

The spacer 130 is connected with the spring 50b when the coils 52b of the spring are spaced apart from each other. In this unactuated condition of the surgical instrument 10b, the flexible stem section 20b has a linear configuration as seen in FIG. 7. The rigid portion 80b of the drive shaft 70b projects from the rigid stem section 18b.

When the deflection control lever (not shown) of the surgical instrument 10b is actuated, the rigid portion 80b of the drive shaft 70b is pulled in a direction 120b toward the handle of the instrument 10b. The rigid portion 80b of the drive shaft 70b slides axially within the rigid stem section 18b, from the position shown in FIG. 7 toward the position shown in FIG. 9.

The force of the axially moving drive shaft portion 80b is transmitted through the flexible portion 90b of the drive shaft 70b and into the shaver assembly 30b. This force is transmitted from the shaver assembly 30b into the distal end portion 54b of the spring 50b.

The axially inwardly directed force on the spring 50b attempts to compress the spring 50b. The spring 50b does compress, but not linearly. Instead, because the spacer 130 places the neutral axis of bending 68b of the spring 50b away from the neutral axis of bending 100b of the flexible portion 90b of the drive shaft 70b, the spring bends away from the spacer as the spring compresses, assuming the bent condition shown in FIG. 3.

The spacer 130 controls the spacing between the coils 52b of the spring 50b as the spring bends. Specifically, the spacing between the coils 52b of the spring 50b does not change at the location 66b where they are attached to the spacer 130. The spacing between the coils 52b of the spring 50b decreases significantly at the opposite side of the spring. The spring 50b shortens along the inside of the arc through which it bends.

The bending of the flexible stem section 20b causes the shaver assembly 30b to be moved to an orientation off the longitudinal central axis 48b. The amount of bending movement of the flexible stem section 20b, and, thus, the position or orientation of the shaver assembly 30b, is controlled by the amount of relative axial displacement between the rigid stem section 18b and the rigid portion 80b of the drive shaft 70b.

Upon movement of the deflection control lever to its initial position, the axial force on the drive shaft 70b is released. The resilience provided by the flexible stem section 20b including the flexible portion 90b of the drive shaft 70b help to return the surgical instrument 10b to its linear condition.

Because the coils 52b of the spring 50b are spaced apart when the surgical instrument 10a is in the linear condition shown in FIG. 7, the surgical instrument 10b can be directed to bend in the opposite direction also. Specifically, if the deflection control lever (not shown) of the surgical instrument 10a is actuated in the opposite direction, so that the rigid portion 80b of the drive shaft is moved in a direction away from the handle 12b, the flexible stem section 20b bends in the opposite direction from FIG. 9, that is, upward as viewed in FIG. 7. The spring 50b then would elongate along the outside of the arc through which it bends.

FIGS. 10 and 11 illustrate a surgical instrument 10c constructed in accordance with a fourth embodiment of the present invention. The surgical instrument 10c is similar in construction and operation to the surgical instrument 10b (FIGS. 7–9). Parts of the surgical instrument 10c which are the same as or similar to corresponding parts of the surgical instrument 10b are given the same reference numeral with the suffix "c" added for clarity.

Like the surgical instrument 10bthe surgical instrument 10c includes a spacer 130c on the spring. The surgical instrument 10c also includes a second spacer 150, which is connected with the flexible portion 90c of the drive shaft 70c. The second spacer 150 is similar in configuration to the first spacer 130 and includes a main body portion 152 which extends along the outer periphery of the turns or coils 91 of the flexible portion 90c of the drive shaft 70c. A plurality of projecting portions 154 in the form of small ribs or fingers extend radially inward from the main body portion 152 of the second spacer 150.

The second spacer 150 extends along the outer periphery of the flexible portion 90c of the drive shaft 70c and overlies the coils 91 of the flexible portion of the drive shaft. Each one of the projecting portions 154 of the second spacer 150 is disposed between, and separates, a pair of adjacent turns 91 of the flexible portion 90c of the drive shaft 70c. The second spacer 150 thus controls the spacing between the turns 91 of the flexible portion 90c of the drive shaft 70c, as the first spacer controls 130 the spacing of the coils 52c of the spring 50c.

The second spacer 150 is connected with the flexible portion 90c of the drive shaft 70c at one particular location 66c around its circumference. In the illustrated embodiment, the second spacer 150 has a circumferential extent of about 25° about the axis 48c. The second spacer 150 is attached to the flexible portion 90c of the drive shaft 70c when the coils 91 are spaced apart from each other. In this unactuated condition of the surgical instrument 10b, the flexible stem section 20c has a linear configuration as seen in FIG. 10.

The surgical instrument 10c can be made to bend in either direction (up or down as viewed in FIG. 10) depending on the direction of the force applied between the inner tubular member (the flexible portion 90c of the drive shaft 70c) and the outer tubular member (the spring 50c). Specifically, if the rigid portion 80c of the drive shaft 70c is pushed in a direction away from the handle (to the right as viewed in FIG. 10) relative to the rigid stem section 18c, the flexible portion 90c of the drive shaft attempts to compress relative to the spring 50c. The distal end of the instrument 10c bends downward as viewed in FIG. 10. On the other hand, if the rigid portion 80c of the drive shaft 70c is pulled in a direction toward the handle (to the left as viewed in FIG. 10) relative to the rigid stem section 18c, then the distal end of the instrument 10c bends upward as viewed in FIG. 10. The use of the second spacer 150 increases the moment arm available at the distal end of the flexible stem section 20c for bending in either direction.

FIGS. 12–14 illustrate a surgical instrument 10d constructed in accordance with a fifth embodiment of the present invention. The instrument 10d includes a surgical tool 160 which includes relatively pivotable parts rather than the relatively rotatable parts of the instruments shown in FIGS. 1–11. The surgical tool 160 includes a fixed part or fixed jaw 162. A movable part or movable jaw 164 is supported on the fixed jaw 1652 for pivotal movement relative to the fixed jaw about a pivot pin 166. An actuator cable 168 is connected with the movable jaw for transmitting force to the movable jaw 164 to move the movable jaw relative to the fixed jaw 162 between an open position as shown in FIGS. 12 and 14 and a closed position (not shown) for effecting cutting or removal of tissue.

The surgical tool 160 is supported on relatively slidable outer and inner tubes 170 and 180 which have distal end portions 172 and 182, respectively, secured to the fixed jaw 162. The tubes 170 and 180 are coaxial and are centered on a longitudinal central axis 174 of the instrument when the instrument 10d is in a linear condition as shown in FIG. 12.

The outer tube 170 is made from a flexible plastic material. The outer tube 170 has a cylindrical configuration including parallel inner and outer side surfaces 176 and 178. The outer tube 170 has a uniform configuration around its circumference and, therefore, its neutral axis of bending is located at the radial center of the outer tube.

The inner tube 180 is preferably made from the same flexible plastic material as the outer tube 170. The inner tube 180 has a cylindrical configuration including parallel inner and outer side surfaces 184 and 186. The inner tube 180 is weakened at predetermined locations along a portion of its length to form a flexible stem section 20d of the instrument 10d. Specifically, a series of ten openings or slots 190 are formed in the upper (as viewed in FIGS. 2 and 3) sector of the inner tube 180. Each one of the slots 190 has a circumferential extent of about 250°.

The slots 190 define a series of nine relatively movable links 192. The links 192 are the sections of the inner tube 180 which are located axially between adjacent slots 190. The slots 190 act as pivot joints or pivot axes between the links 192. The links 192 are pivotally interconnected by the material of the inner tube 180 which is not cut away at the slots 190. The pivotal interconnection of the links 192 enables controlled movement of the surgical tool 160 to a plurality of positions off the axis 174 as illustrated, for example, in FIG. 14.

The slotting of the inner tube 180 varies the bending resistance of the flexible stem section 20d in a predetermined manner. Specifically, the bending resistance of the inner tube 180 and, thereby, of the flexible stem section 20d, is decreased at the location of each one of the slots 190. The neutral axis of bending of the inner tube 180 is located at the material of the inner tube which is not cut away at the slots 190, generally in the area indicated at 194.

When the outer tube 170 is pulled to the left as viewed in FIG. 12, relative to the inner tube 180, the inner tube compresses along its slotted side. The unslotted side (at the neutral axis of bending 194) neither compresses nor extends. The flexible stem section 20d of the surgical instrument 10d bends in the manner shown in FIG. 14. Conversely, when the outer tube 170 is pushed outward relative to the inner tube 180 (to the right as viewed in FIG. 12), the flexible stem 20d section bends in the opposite manner (not shown).

FIGS. 15–18 illustrate a surgical instrument 10e constructed in accordance with a sixth embodiment of the present invention. The surgical instrument 10e is similar in construction and operation to the surgical instrument 10d (FIGS. 12–14). Parts of the surgical instrument 10e which are the same as or similar to corresponding parts of the surgical instrument 10d are given the same reference numeral with the suffix "e" added for clarity.

Like the surgical instrument 10d, the surgical instrument 10e includes a slotted inner tube 180e. The surgical instrument 10e also includes a slotted outer tube 170e. The outer tube 170e is weakened at predetermined locations along a portion of its length to form a portion of the flexible stem section 20e of the instrument 10e. Specifically, a series of eight openings or slots 200 are formed in the lower (as viewed in FIGS. 15–18) sector of the outer tube 170e. Each one of the slots 200 has a circumferential extent of about 250°.

The slots 200 define a series of seven relatively movable links 202. The links 202 are the sections of the outer tube 170e which are located axially between adjacent slots 200. The slots 200 act as pivot joints or pivot axes between the links 202. The links 202 are pivotally interconnected by the material of the outer tube 170e which is not cut away at the slots 200.

The slotting of the outer tube 170e varies the bending resistance of the flexible stem section 20e in a predetermined manner. Specifically, the bending resistance of the outer tube 170e and, thereby, of the flexible stem section 20e, is decreased at the location of each one of the slots 200. The neutral axis of bending of the outer tube 170e is located at the material of the outer tube which is not cut away at the slots 200, generally in the area indicated at 204.

The flexible stem section 20e bends in the same directions upon relative axial movement of the inner and outer tubes 180e and 170e, as does the flexible stem section 20d of the instrument 10d (FIGS. 12–14). The slotting of the outer tube 170e increases the moment arm available at the distal end of the flexible stem section 20e for bending in either direction.

It should be understood that the deflection control assembly 16 is illustrated only schematically. Other types of deflection control assemblies can be substituted. Thus, the deflection control assembly 16 is illustrative of the various types of deflection control assemblies which can be used to provide the force for bending the flexible stem section 24 of the surgical instrument 10 in the manner illustrated.

From the above description of the invention, those skilled in the art will perceive improvements, changes and modifications in the invention. For example, the surgical instrument 10 can include a different type of surgical tool which has a movable part and a fixed part. For example, any one of the flexible stem sections may be usable with a different kind of surgical instrument, such as an instrument with one or more rotating parts or an instrument with one or more pivotable parts. Also, the surgical instrument could be of the type having no moving parts, such as a suction tool. Such improvements, changes and modifications within the skill of the art are intended to be covered by the appended claims.

Having described the invention, we claim:

1. A surgical instrument comprising:

a handle;

a rigid stem section extending from said handle, said rigid stem section defining a longitudinal axis of said surgical instrument;

a flexible stem section extending from said rigid stem section;

said flexible stem section comprising a bendable outer helically coiled spring and a bendable inner helically coiled spring slidably and concentrically disposed within said outer spring; and means connected with a first one of said inner and outer springs for causing said first spring and, thereby, said flexible stem section to bend in a predetermined direction in response to relative axial movement between said inner and outer springs.

2. A surgical instrument as set forth in claim 1 wherein said means for causing bending of said flexible stem section comprises a member connected with said first spring for controlling spacing between adjacent coils of said first spring.

3. A surgical instrument as set forth in claim 2 wherein said member comprises a strap fixed to a plurality of coils of said first spring and extending along the outer periphery of said first spring.

4. A surgical instrument as set forth in claim 2 wherein said member comprises a spacer having portions extending radially between adjacent coils of said first spring.

5. A surgical instrument as set forth in claim 4 wherein said spacer portions extend between adjacent coils of said outer spring.

6. A surgical instrument as set forth in claim 4 wherein said spacer portions extend between adjacent coils of said inner spring.

7. A surgical instrument as set forth in claim 1 wherein said means for causing bending of said flexible stem section comprises a member which defines a neutral axis of bending of said first spring, the second one of said inner and outer springs having a neutral axis of bending spaced apart from the neutral axis of bending of said first spring.

8. A surgical instrument as set forth in claim 1 wherein said means for causing bending of said flexible stem section comprises means for blocking axial movement between adjacent coils of said first spring at a selected location along the circumference of said first spring during bending movement of said first spring.

9. A surgical instrument as set forth in claim 1 wherein said first spring is an extension spring having its coils in abutting engagement when said first spring is in a linear condition.

10. A surgical instrument as set forth in claim 1 wherein said inner spring comprises a flexible drive shaft.

11. A surgical instrument comprising:

a handle;

a rigid stem section extending from said handle, said rigid stem section defining a longitudinal axis of said surgical instrument; and a flexible stem section extending from said rigid stem section;

said flexible stem section comprising a bendable outer tubular member and a bendable inner tubular member slidably and concentrically disposed within said outer tubular member, said outer tubular member having a neutral axis of bending, said inner tubular member having a neutral axis of bending spaced apart from the neutral axis of bending of said outer tubular member;

said flexible stem section being movable between a plurality of orientations relative to said axis in response to relative sliding movement between said inner and outer tubular members.

12. A surgical instrument as set forth in claim 11 wherein said bendable outer member comprises a coiled spring.

13. A surgical instrument as set forth in claim 12 wherein said bendable inner member comprises a flexible drive shaft.

14. A surgical instrument as set forth in claim 11 wherein said bendable inner member comprises a flexible drive shaft.

15. A surgical instrument as set forth in claim 11 wherein said bendable outer member is weakened at predetermined locations spaced apart along the length of said outer member for decreasing the bending resistance of said outer member at said predetermined locations.

16. A surgical instrument as set forth in claim 15 wherein said outer member has a plurality of slots which decrease the bending resistance of said outer member at said predetermined locations.

17. A surgical instrument as set forth in claim 11 wherein said bendable inner member is weakened at predetermined locations spaced apart along the length of said inner member for decreasing the bending resistance of said inner member at said predetermined locations.

18. A surgical instrument as set forth in claim 17 wherein said inner member has a plurality of slots which decrease the bending resistance of said inner member at said predetermined locations.

19. A surgical instrument as set forth in claim 17 wherein said bendable outer member is weakened at predetermined locations spaced apart along the length of said outer member for decreasing the bending resistance of said outer member at said predetermined locations.

* * * * *